US 11,058,347 B2

(12) United States Patent
Jia et al.

(10) Patent No.: US 11,058,347 B2
(45) Date of Patent: Jul. 13, 2021

(54) DEVICE FOR THE DETECTION AND PREVENTION OF PRESSURE ULCERS AND METHODS OF USE

(71) Applicant: BOARD OF REGENTS, THE UNIVERSITY OF TEXAS SYSTEM, Austin, TX (US)

(72) Inventors: U-Ter Aondo Grace Jia, San Antonio, TX (US); Meryem Bousfiha, San Antonio, TX (US); Casey Whitney, San Antonio, TX (US); Mario Hernandez, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 409 days.

(21) Appl. No.: 15/961,091

(22) Filed: Apr. 24, 2018

(65) Prior Publication Data
US 2018/0303407 A1    Oct. 25, 2018

Related U.S. Application Data

(60) Provisional application No. 62/489,424, filed on Apr. 24, 2017.

(51) Int. Cl.
| *A61B 5/00* | (2006.01) |
| *A61G 7/057* | (2006.01) |
| *A61B 5/103* | (2006.01) |

(52) U.S. Cl.
CPC ............ *A61B 5/447* (2013.01); *A61B 5/1032* (2013.01); *A61B 5/6804* (2013.01); *A61B 5/688* (2013.01);
(Continued)

(58) Field of Classification Search
CPC ..... A61B 5/447; A61B 5/1032; A61B 5/6804; A61B 5/6831; A61B 5/6843; A61B 5/688; A61B 5/7225; A61B 5/7275; A61B 5/746–747; A61B 2562/0247; A61G 2203/34; A61G 7/057
(Continued)

(56) References Cited

U.S. PATENT DOCUMENTS

| 3,911,425 A | 10/1975 | Muncheryan ................. 340/326 |
| 4,554,930 A | 11/1985 | Kress ............................ 128/774 |

(Continued)

FOREIGN PATENT DOCUMENTS

| EP | 2378968 | 4/2016 | ............. A61B 5/103 |

OTHER PUBLICATIONS

Hmel, PJ, et al, "Physical and thermal properties of blood storage bags: implications for shipping frozen components on dry ice," Department of Blood Research, Walter Reed Army Institute of Research, Silver Spring, MD 20910-7500, (Jul. 24, 2002).
(Continued)

*Primary Examiner* — Daniel L Cerioni
*Assistant Examiner* — Raymond P Dulman
(74) *Attorney, Agent, or Firm* — David G. Rosenbaum; Rosenbaum IP

(57) ABSTRACT

Provided herein are systems, methods and devices for the Detection and Prevention of Pressure Ulcers. The system, methods, and devices generally relate to sensors and fluid systems for detecting ulcers and preventing further pain for the patient and allow healthcare providers with valuable information to reposition a patient.

20 Claims, 11 Drawing Sheets

(52) U.S. Cl.
CPC .......... *A61B 5/6831* (2013.01); *A61B 5/6843* (2013.01); *A61B 5/6892* (2013.01); *A61B 5/7225* (2013.01); *A61B 5/7275* (2013.01); *A61B 5/746* (2013.01); *A61B 5/747* (2013.01); *A61G 7/057* (2013.01); *A61B 2562/0214* (2013.01); *A61B 2562/0247* (2013.01); *A61B 2562/0252* (2013.01); *A61B 2562/046* (2013.01); *A61G 2203/34* (2013.01)

(58) Field of Classification Search
USPC ........................................................ 600/587
See application file for complete search history.

(56) References Cited

U.S. PATENT DOCUMENTS

| | | | | |
|---|---|---|---|---|
| 4,862,730 | A | 9/1989 | Crosby | 73/38 |
| 5,202,091 | A | 4/1993 | Lisenbee | 422/52 |
| 6,287,253 | B1 | 9/2001 | Ortega et al. | 600/300 |
| 7,378,975 | B1 | 5/2008 | Smith et al. | 340/573.1 |
| 8,011,041 | B2 | 9/2011 | Hann | 5/652.1 |
| 8,116,838 | B2 | 2/2012 | Gaspard et al. | 600/322 |
| 8,301,219 | B2 | 10/2012 | Chen et al. | 600/393 |
| 8,558,702 | B2 | 10/2013 | Smith et al. | 340/573.1 |
| 2005/0004500 | A1 | 1/2005 | Rosser et al. | 128/889 |
| 2006/0064800 | A1 | 3/2006 | Freund | 2/446 |
| 2008/0171383 | A1* | 7/2008 | Selker | C12M 41/34 435/288.7 |
| 2009/0260639 | A1 | 10/2009 | Hsu et al. | 128/888 |
| 2012/0330112 | A1* | 12/2012 | Lamego | A61B 5/02225 600/301 |
| 2015/0174304 | A1* | 6/2015 | Askem | A61M 1/0027 604/319 |

OTHER PUBLICATIONS

ASTM D 1623-09, "Standard Test Method for Tensile and Tensile Adhesion Properties of Rigid Cellular Plastics," ASTM International, West Conshohocken, PA, (2009) www.astm.org.

Hucker, G.J., et al. "Methods of Gram Staining," Technical Bulletin No. 93, New York Agricultural Experiment Station, Geneva NY, (Mar. 1923).

Ashley, R.J. "Permeability and Plastics Packaging," In: Comyn J. (eds) Polymer Permeability, pp. 269-308, Springer, Dordrecht (1985).

Haberle, J.G., et al., "An improved technique for compression testing of unidirectional fibre-reinforced plastics; development and results." Composites, vol. 25, Issue 5, pp. 358-371, Department of Aeronautics, Imperial College of Science, Technology and Medicine, Prince Consort Road, London SW7 2BY, UK (May 1994).

Xiao, X. "Dynamic tensile testing of plastic materials." Polymer Testing, vol. 27, Issue 2, pp. 164-178, General Motors Corporation, MC 480-106-710, 30500 Mound Road, Warren, MI 48090-9055, USA (Apr. 2008).

Molnar, M., et al. "Laboratory testing of biodegradation in soil." Land Contamination and Reclamation 17.3-4, pp. 495-506 (Nov. 2009).

\* cited by examiner

| Component | Function | Potential Failure Mode | Potential Effect of Failure | Potential Cause of Failure | Severity | Probability of Occurrence | Design Controls | Detection | Risk of Occurrence |
|---|---|---|---|---|---|---|---|---|---|
| Cap | Detects pressure | Inability to open | No colorimetric or fluorescence change | Assembly error, inaccurate weight classing | Critical | Remote | Assembly instructions and labeling, weight class matching | Marginal | Improbable |
| Fluid Reservoir | Holds fluid and transmits pressure through fluid | Burst; leak | Insufficient pressure transmission to valves | Puncture, inaccurate weight classing, environmental damage, mishandling | Critical | Occasional | Material choice, impact resistant packaging, weight class matching, real time aging studies | Marginal | Improbable |
| Valve | Transmits fluid to valve and collection, contains fluorescent reaction | Reaction does not occur, fluid is not transmitted | No colorimetric or fluorescent change | Assembly error, insufficient chemical coating, application error | Marginal | Occasional | Assembly instructions, real time aging | Negligible | Improbable |
| Collection | Display color change and fluorescence | Burst; leak | Color change is not displayed or contained | Packaging and storage errors, excess weight | Critical | Occasional | Material choice, impact resistant packaging, weight class matching | Marginal | Improbable |

FIG. 7

| Potential Failure | Cause of Failure | Failing Criteria | Probability of Occurrence | Severity of Cost | Risk Level | Control Type | Control Method |
|---|---|---|---|---|---|---|---|
| | Device Leakage | Ingestion, skin contact | Improbable | Critical | III | Education on device safety and proper application | Handling and application instructions |
| | Device impermeability | Slow skin healing and aeration as risk site | Probable | Critical | I | Material replacement | Replacement with polyurethane |
| | Ingestion | Ingestion, prolonged direct skin contact | Impossible | Critical | IV | Education on device safety and proper application | Handling and application instructions |
| | Improper fastening and application | Tube wraps around patient's neck | Improbable | Critical | III | Education on device safety and proper application | Handling and application instructions |
| | Prolonged device contact with patient's skin, improper fastening and application | Movement of patient's skin relative to stationary device | Probable | Marginal | II | Education on device safety and proper application | Application of devices to clothes and bed, not directly to skin |
| | Mechanical failure of device | Valve is irresponsive to pressure increase | Improbable | Marginal | IV | Alternative pressure valve options | Use of fluid dam as a replacement for check valve system |
| | Valve pressure on the skin | Bulky valve increases pressure on skin and compromised skin healing | Probable | Marginal | II | Design Adjustment | Reduced valve dimension |
| | Device impermeability | Insufficient moisture transport from skin through | Probable | Marginal | II | Education on device safety and proper application | Timed usage, intermediate breaks between application |

DEVICE FOR THE DETECTION AND PREVENTION OF PRESSURE ULCERS AND METHODS OF USE

CROSS-REFERENCE TO RELATED APPLICATIONS

The present applications claims priority from U.S. provisional application Ser. No. 62/489,424, filed Apr. 24, 2017, herein incorporated by reference in its entirety.

BACKGROUND

The invention generally relates to apparatus and method for the prevention of pressure Sores.

Pressure ulcers are a common complication in sedentary patients and currently affects around 3 million adults in the United States. The injury occurs as a result of prolonged or intense pressure, leading to hypoxia of the tissue and localized tissue death. Treatment is very costly and care for pressure ulcers average at $37,800. Prevention of pressure ulcer is therefore necessary. Healthcare's current gold standard for prevention of an ulcer is to reposition sedentary patients every 2 hours; this becomes a feasibility issue in hospitals with large patient to nurse ratio. Furthermore, it is the combination of weight, time, and risk which account for pressure ulcer development. These factors vary in severity from patient to patient.

The present invention attempts to solve these problems, as well as others.

SUMMARY OF THE INVENTION

Provided herein are systems, methods and devices for the Detection and Prevention of Pressure Ulcers. Generally speaking in one embodiment, the device for the detection and prevention of pressure ulcers, comprises: a fluid chamber operably coupled with a valve member and a tube member, and the fluid chamber including a fluid and the fluid chamber is positioned between a patient and another surface; the valve member including a first valve and a second valve, wherein the first valve opens as fluid pressure builds within the fluid chamber, the first valve releasing the fluid through the tube member to the second valve at a pressure threshold; the second valve opens at a pressure threshold after a first time period to release the fluid to the tube member; and the fluid displays a color once the pressure threshold is reached and the fluid is released from the second valve.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 7 is a table of the Failure Mode and Effects Analysis showing the risks experienced by the different component parts of the device, and the outcome in probability and severity as those risks are addressed.

FIG. 8 is a table showing the hazards that are posed to the patient as a result of device use and control means.

DETAILED DESCRIPTION OF THE INVENTION

Figure 1A:
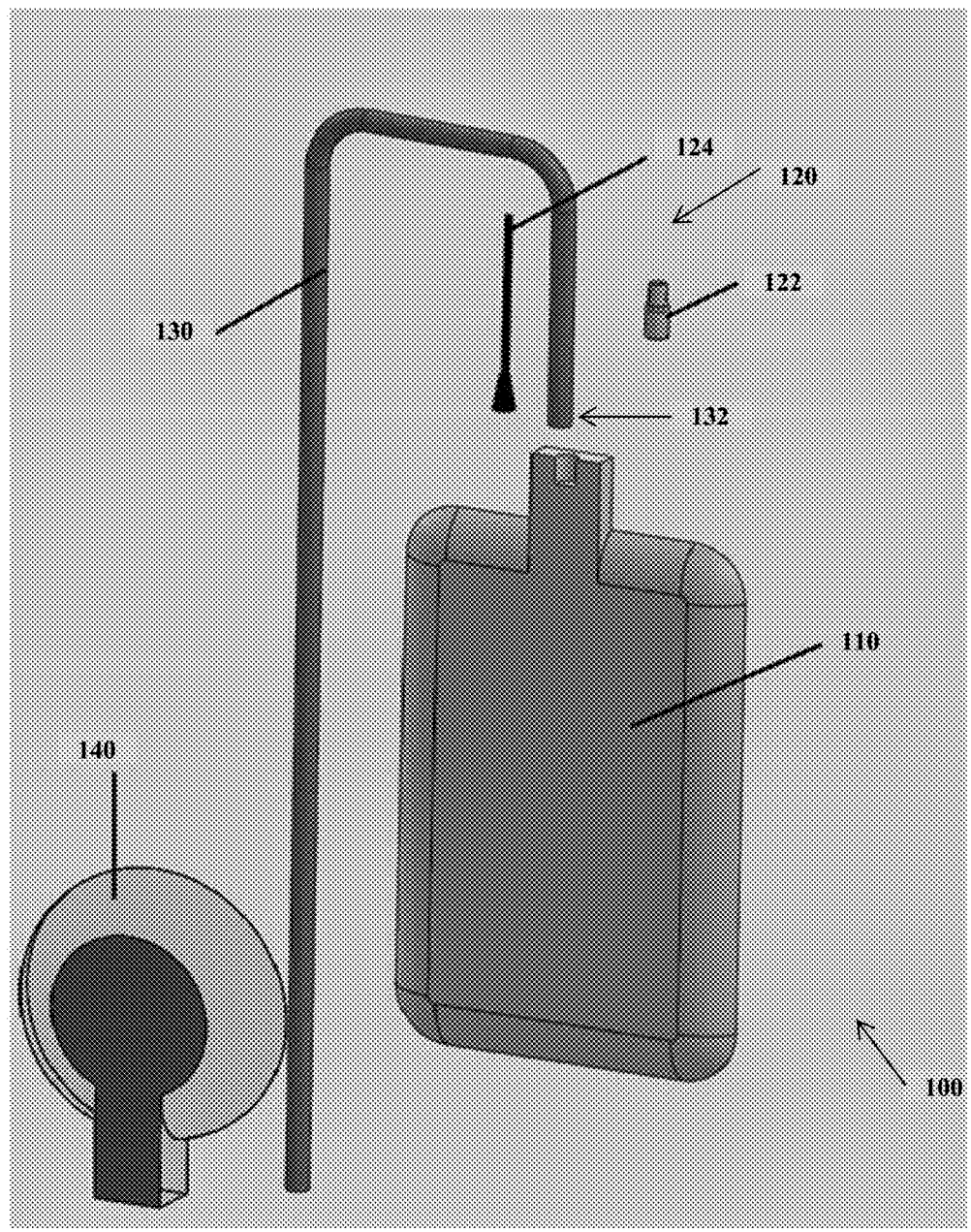
FIG. 1A is an exploded view of one embodiment of the device.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, biological, biochemical and medical arts.

Generally speaking, a device that can detect and prevent the formation of pressure ulcers in multiple sites of the body is disclosed. In one embodiment, the device is used in the absence of electricity. The device senses the prolonged or intense pressure that is causal in development of a pressure ulcer. As shown in FIG. 1A, and in one embodiment, the device 100 comprises a fluid chamber 110 operably coupled with a valve 120, and the fluid chamber 110 includes a fluid that chemiluminescences or displays a color once a pressure threshold is reached. The fluid chamber 110 is positioned between the patient and the bed. The valve member 120 includes a first valve 122 and a second valve 124, where the first valve 122 serves as a mini-check valve. As pressure builds within the fluid chamber 110, the force exerted on the first valve 122 causes it to open, releasing the fluid through the tube 130 to the second valve 124. The second valve 130 opens at a pressure threshold of about 35 mmHg, where about 35 mmHg is about 50% of pressure that causes the formation of a pressure ulcer. The second valve 124 is a downstream inline valve that is time dependent and restricts flow velocity of the fluid after leaving the first valve 122. The device restricts flow to 50% time required to form the ulcer. Fluid collects in a collection member 140 will fluoresce in low light conditions and be apparent as a bright color otherwise. This warning indication will allow healthcare providers with valuable information to reposition a patient, therefore preventing the development of a pressure ulcer.

Figure 2:
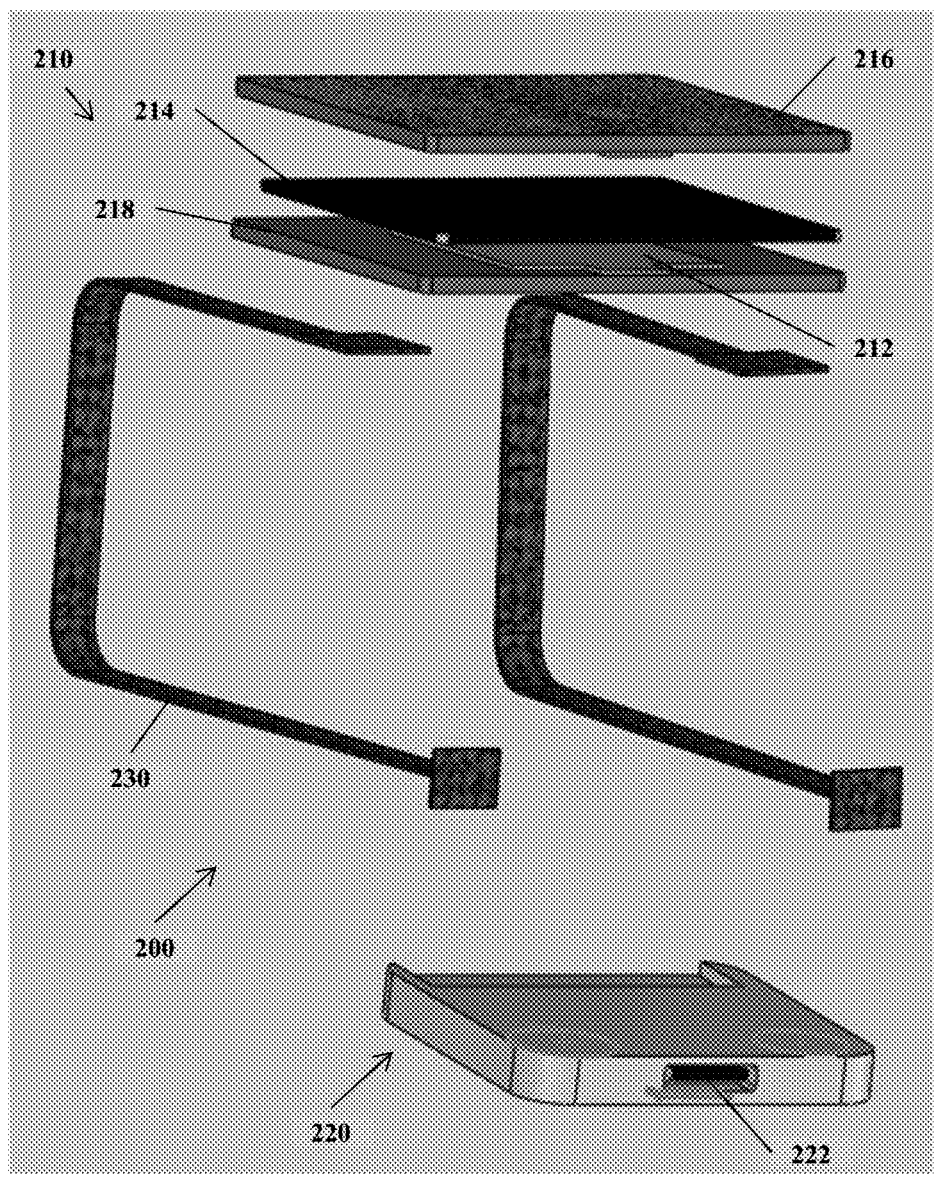
FIG. 2 is an exploded view of another embodiment of the device.

As shown in FIG. 2, in another embodiment, the device 200 addresses an ulcer patients skin integrity issue by avoiding contact with the dermis altogether. The device 200 comprises a first unit 210 operably coupled to an alarm unit 220. The first unit 210 includes a pressure sensor 212, which is extremely flat and securely attaches to the patient's hospital gown at the pressure point of interest by an attachment mechanism 230. In one embodiment, the pressure sensor 212 is made of velostat, a piezoresistive material, sandwiched between conductive fabric 214 sewn onto a nonconductive fabric 216. When pressure is applied, the piezoresistive material sends a mV signal is to the alarm unit 220; the unit 220 is set to a predetermined pressure/time limit depending on the patient and will let out an alarm of >80 db to notify the healthcare giver after a limit has been exceeded. This pressure/time value will change depending on a patient's needs and can be varied by a program transferred via a usb port 22 included within the device. Alternatively, the program may be transferred or transmitted wirelessly, such as with Bluetooth, the IEEE 802.11 standard, Wi-Fi, broadband wireless, and/or any wireless communication that can be accomplished using radio frequency communication, microwave communication, and infrared communication. Around the patient and connecting the two units wraps more conductive fabric encased in nonconductive fabric, also securely attached to the patient's hospital gown. While the alarm unit is reusable and durable, the pressure sensor is detachable and disposable.

Piezoresistive materials are materials that change resistance to the flow of current when they are compressed or strained. Most pressure sensors use the semiconductor silicon. When force is put on the silicon, it becomes more resistant to a current pushing through. This resistance is usually very linear—twice as much pressure results in twice as large a change in resistance. A Piezoresistive Pressure Sensor contains several thin wafers of silicon embedded between protective surfaces. The surface is usually connected to a Wheatstone bridge, a device for detecting small differences in resistance. The Wheatstone bridge runs a small amount of current through the sensor. When the resistance changes, less current passes through the pressure sensor. The Wheatstone bridge detects this change and reports a change in pressure. Uses the piezoresistive effect of bonded or formed strain gauges to detect strain due to applied pressure, resistance increasing as pressure deforms the material. Common technology types are Silicon (Monocrystalline), Polysilicon Thin Film, Bonded Metal Foil, Thick Film, and Sputtered Thin Film. Generally, the strain gauges are connected to form a Wheatstone bridge circuit to maximize the output of the sensor and to reduce sensitivity to errors. This is the most commonly employed sensing technology for general purpose pressure measurement.

Alternative pressure sensors include force collector types. These types of electronic pressure sensors generally use a force collector (such a diaphragm, piston, bourdon tube, or bellows) to measure strain (or deflection) due to applied force over an area (pressure). Capacitive sensors uses a diaphragm and pressure cavity to create a variable capacitor to detect strain due to applied pressure, capacitance decreasing as pressure deforms the diaphragm. Common technologies use metal, ceramic, and silicon diaphragms. Electromagnetic sensors measure the displacement of a diaphragm by means of changes in inductance (reluctance), LVDT, Hall Effect, or by eddy current principle. Optical sensors include the use of the physical change of an optical fiber to detect strain due to applied pressure. A common example of this type utilizes Fiber Bragg Gratings. This technology is employed in challenging applications where the measurement may be highly remote, under high temperature, or may benefit from technologies inherently immune to electromagnetic interference. Another analogous technique utilizes an elastic film constructed in layers that can change reflected wavelengths according to the applied pressure (strain). Potentiometric sensors uses the motion of a wiper along a resistive mechanism to detect the strain caused by applied pressure.

Figure 3A:
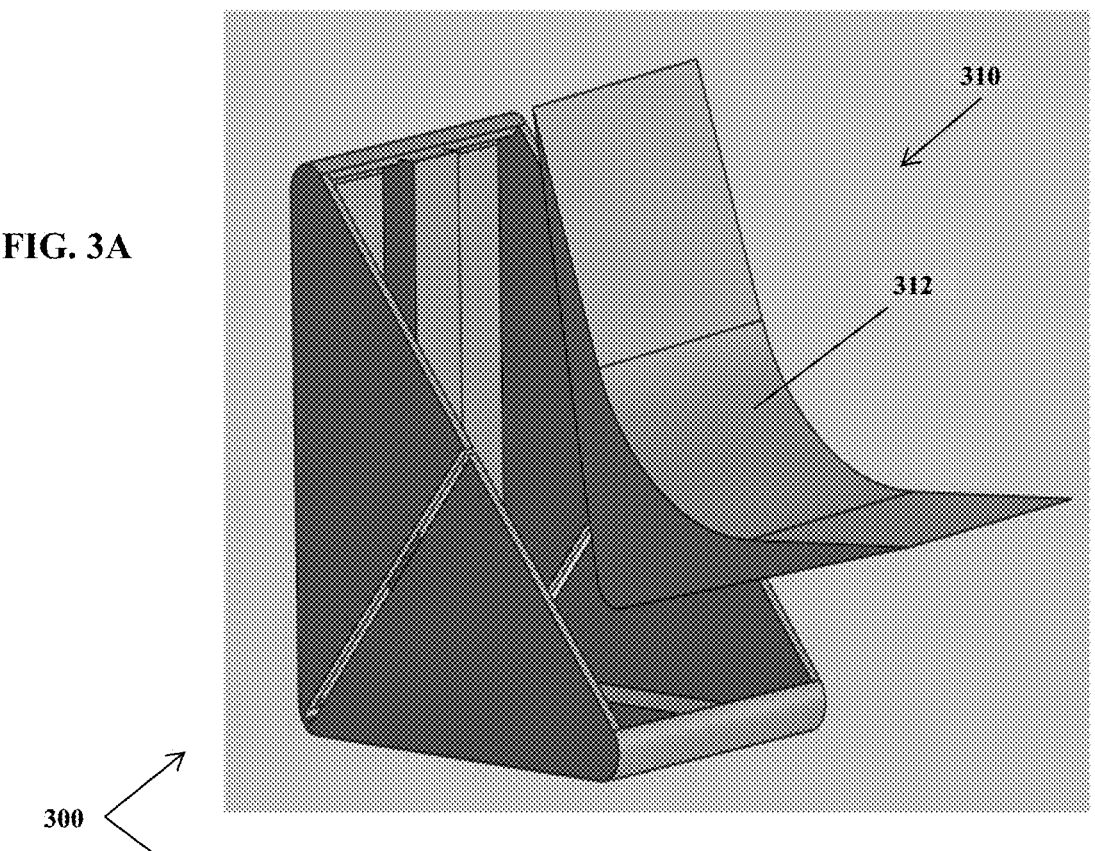
FIG. 3A is an exploded view of another embodiment of the device.
Figure 3B:
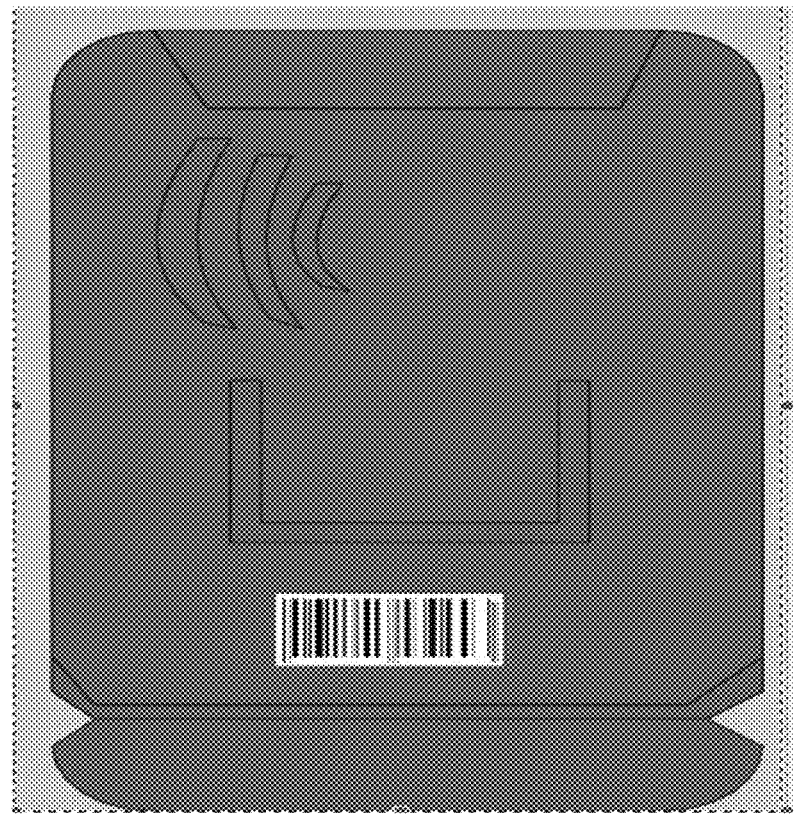
FIG. 3B is a bottom view of the alarming sensing unit, in one embodiment of the device.

As shown in FIG. 3, in another embodiment, the device 300 continuously measures the pressure on the patient's skin. The device 300 comprises a monitoring device 310 operably coupled to an alarm system 320. The monitoring device 310 includes a pressure sensor 312 that senses the pressure exerted on the skin and records the elapsed time. When the pressure reaches a predetermined level, the alarm system 320 will audibly alert the patient that he/she needs to be repositioned. Once the patient is repositioned, the timer resets due to the absence of pressure that the pressure sensor will sense. The device allows the reading of the actual pressure on the skin since it's in direct contact with the skin.

The monitoring device 310 includes a microprocessor and a timer to monitor the pressure the skin has been exposed to. In one embodiment, the pressure sensor used will be an IC Piezoresistive pressure sensor that measures pressure from about 5 mmHg to about 100 mmHg. The number of pressure sensors will vary on the position of the wound dressing. It will connect to the microprocessor which also receives input from a timing device. The microprocessor determines whether the pressure and elapsed time leads to irreversible skin damage and alerts the patient.

In one embodiment, the pressure sensors and timing device are enclosed in a wound dressing made out of polyurethane foam dressing. The wound dressing includes different shapes and sizes depending on the body location. Each wound dressing includes a barcode that will be scanned by the alarming device. Prior to the use of the wound dressing, the caregiver will scan the wound dressings used on the alarming device. The alarming device will detect and continually monitor the increase in pressure. Once it reaches a certain threshold, it will make an audible noise (>about 80 dB) to alarm the patient. The patient will then alert the caregiver so he/she could be repositioned. The alarming system could be reused, whereas the wound dressings and pressure sensors are disposable.

Polyurethane foam dressing will also prevent the formation of the pressure ulcer. It absorbs moisture and prevents leakages, which in turn reduces the risk of maceration. It will also provide a barrier to the penetration of bacteria.

Figure 4:
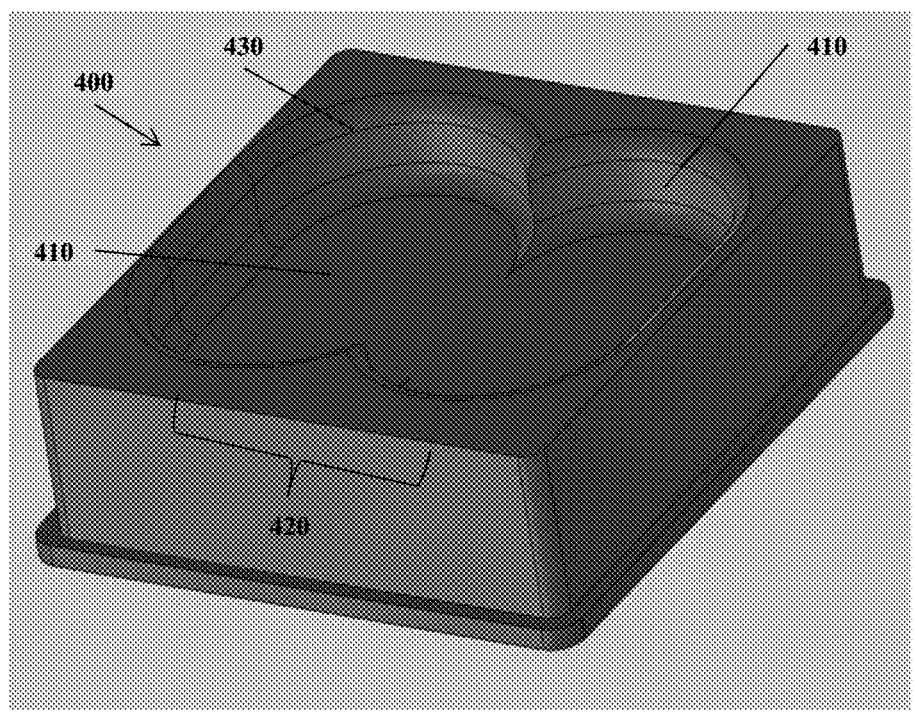
FIG. 4 is a perspective view of another embodiment of the device.

As shown in FIG. 4, in another embodiment, the device 400 distributes the pressure that is usually concentrated in the center of the wheel seat of a patient. The device 400 distributes the pressure by including at least two depressions 410 in the middle of the device. The primary distribution of the pressure caused by the weight of the user will be better distributed since the middle section 420 of the device will not have a direct contact with the surface of the seat. The best angle 430 for the best distribution is between at least 10 degrees and at least 80 degrees. Also, the at least two depressions 410 are created to better fit the limbs of wheelchair users that for any reason have lost them. In one embodiment, the surface is a memory foam which is a soft and deformable material. Memory foam consists mainly of polyurethane as well as additional chemicals increasing its viscosity and density of the foam. Memory foam is a viscoelastic polyurethane foam, or low-resilience polyurethane foam (LRPu). Higher-density memory foam softens in reaction to body heat, allowing it to mold to a warm body in a few minutes. To reduce the occurrence of the ulcer the upper part of the memory foam will be covered by a Microclimate Body Pad. This Microclimate Body Pad is proved to prevent the formation of the ulcers due to its softness and its ability to keep a cool temperature regardless of the tissue/material contact for extended periods.

Figure 1B:
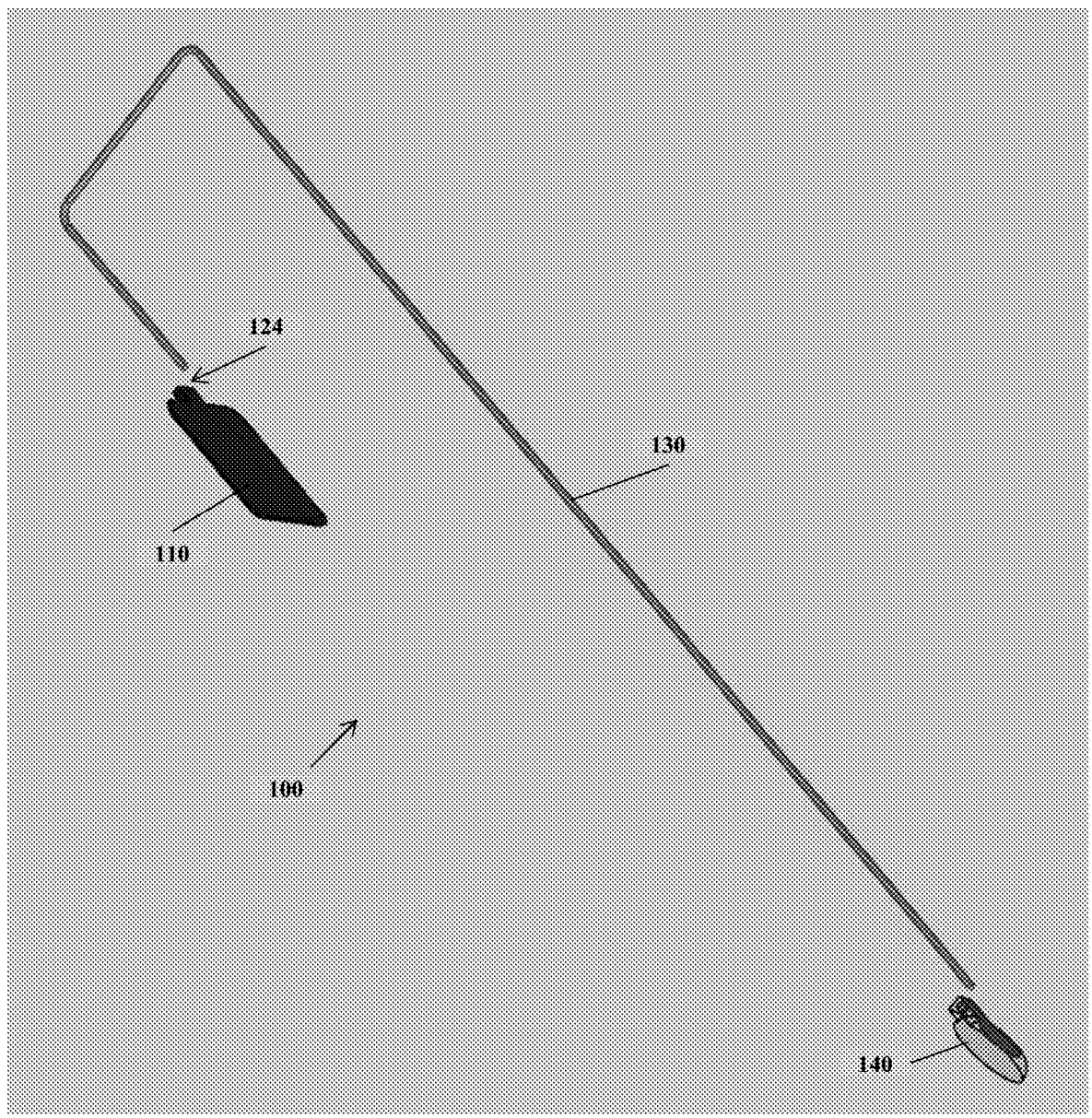
FIG. 1B is a perspective view of one embodiment of the device.

As shown in FIGS. 1A-1B, in another embodiment, the device 100 comprising the fluid member 110 operably coupled to the valve member 120, and the tube member 130 operably coupled with the collection member 140. In one embodiment, the fluid member 110 contains a fluorophore which is a chemiluminescent agent. The fluid member 110 is attached to the clothes, bed or wheelchair seat of the patient. The fluid member 110 may be fastened by an attachment mechanism, such as a temporary adhesive, clip, belt, or other mechanism described below. In one embodiment, the tube member 130 is placed along the back of the patient, so that the collection member 140 hangs over the shoulder. In one embodiment, the collection member 140 is fastened to the front of the patient using a temporary adhesive, clip, belt, or other attachment mechanism. As pressure builds within the fluid member 110 beneath the patient, at the risk site (reflective of the pressure building on the skin and underlying tissue) the force on the fluid member 110 and transmitted through the fluid is exerted on the first valve member 122 of the valve member 120 causing it to open. The fluid is then released through the tube 130 to the second valve member 124, which includes a time sensing part of the valve to collect in the collection member 140. The second valve member 124 is the time dependent pressure sensing mechanism of the device releasing the fluid at a first time period. In alternative embodiment, the valve member 120 is operably coupled to an alarm system as to not require the tube or collection member with a chemiluminescent agent in the fluid, as described above.

A valve is a device that regulates, directs or controls the flow of a fluid (gases, liquids, fluidized solids, or slurries) by opening, closing, or partially obstructing various passageways. A check valve, clack valve, non-return valve, reflux valve, retention valve or one-way valve is a valve that normally allows fluid (liquid or gas) to flow through it in only one direction. Check valves are two-port valves, meaning they have two openings in the body, one for fluid to enter and the other for fluid to leave. An important concept in check valves is the cracking pressure which is the minimum upstream pressure at which the valve will operate. Typically the check valve is designed for and can therefore be specified for a specific cracking pressure. In one embodiment, the first valve is a check valve and includes a cracking pressure of at least about 1 mmHG to about 20 mmHg. Alternatively, the first valve is a valve ball and can also be made of different types of plastic, such as ABS, PVC, PP or PVDF.

An alternative approach to the first valve member is a fluid dam. A dam would be formed using glue to secure a small disc of glass over the entrance 132 of the tube 130, as shown in FIG. 1B. The dam would separate the fluid in the fluid member 130 from the tube 130, and open to release fluid to the collection member 140 when predetermined pressure and time values are reached. This alternative is reserved as a viable option depending strictly on the failure of the initially proposed valve member. Breaking the dam to release fluid into the tube member from the fluid member depends on the bond strength of the glue holding the glass disc. The pressure sensing mechanism of the glass dam is the bond strength that corresponds to the release pressure of the device. Hence, the dam would have to break at a force matches the selected about 35 mmHg of pressure (the breaking pressure can be determined as needed). This would be done by adjusting the surface area of the dam, because pressure is the amount of force applied over a certain area.

In one embodiment, the first valve 122 opens at a pressure threshold of about 35 mmHg (50% of pressure that causes the formation of a pressure ulcer), in a first time period of about 30 mins (~50% time required to form the ulcer). Alternative time periods may be between about 10 minutes to about 60 minutes if the pressure is altered and depending upon the sensitivity to ulcer development or weight of the patient. Alternative time periods may be greater than about 60 minutes, alternatively, between about 30 minutes and 360 minutes, between about 10 minutes and 240 minutes, between about 15 minutes and 180 minutes. Alternative pressure thresholds may be between about 5 mmHg to about 75 mmHg depending on the sensitivity to ulcer development or the weight of the patient. Alternative pressure thresholds may be between 10 mmHg and about 60 mmHg, alternatively, between about 15 mmHg and about 50 mmHg, alternatively between about 20 mmHg and about 40 mmHg. For instance, if the patient's skin is vulnerable to ulcer development, then the pressure threshold may be decreased to below 30 mmHg and the time period may also be decreased to below about 25 minutes. If the patient is lighter in weight or has a BMI below 18.5, then the pressure threshold may be increased to above 35 mmHg or the time period may be increased to above 30 minutes. Location and placement of the fluid member may also factor in the pressure threshold and time period of the first valve and the second valve. For instance, if the fluid member can only be placed in an area of the patient that has a lower body mass or is mostly a bony area, then the pressure threshold may be decreased to sense the lower threshold for developing ulcers in that particular area. Alternatively, if the fluid member can only be placed in an area of the patient that has a high body mass or fat content, then the pressure threshold may be decreased to accommodate the higher pressure for the development of ulcers. Comorbidities could contribute to the comprised integrity of the patient's skin, increasing their risk for pressure ulcer formation, such as diabetes. In such cases, the pressure threshold could also be decreased, to accommodate the higher risk.

In one embodiment, the time dependent inline second valve member 124 follows the first valve member 122 is a reduction in the diameter of the outlet tube from the preceding first valve. The restriction in diameter allows control of the velocity of fluid flow. Control of the flow velocity allows indirect control of the flow time. Hence, the fluid flow can be calculated for and used to design the time valve such that the once fluid crosses the pressure valve, it requires a predetermined time period (about 30 mins) to travel to the collection member where it is visible. In one embodiment, the inline valve is a device that regulate the flow of gases, fluids or materials through a structure or aperture by opening, closing or obstructing a port or passageway.

In one embodiment, the device is disposable. After the valve is opened (or the glue dam that holds the glass is deformed destructively, in the case of the alternative) it is no longer able to restrict fluid flow and ineffective for sensing further pressure builds up. Fluid collected in the collection member 140 indicates that the pressure has exceeded the allowable threshold of the seal (valve or dam), and that without changing the patient's position, the increasing pressure would cause the formation of an ulcer. The mechanism of the glue is subject to change, as result of the time dependency of pressure ulcer formation that is not accommodated by the deformation of glue. Alternatively, the device is reusable where the fluid in the collection member may be drained and the first valve and the second valve are reset along with new fluid in the fluid member. Secured openings/closings on the fluid member and the collection member may allow for the fluid disposable and reloading.

In one embodiment, the fluid within the fluid member is a fluorophore or chemical that undergoes chemiluminescence, which is the emission of light (luminescence), as the result of a chemical reaction. In one embodiment, the fluorophore is phenyl oxalate ester. The tube 130 and collection member 140 are coated with hydrogen peroxide which is the activating agent. A reaction occurs between the fluorophore and hydrogen peroxide, causing fluorescence and a glow in the dark effect. This process is called chemiluminescence allows the pressure sensing to be conducted in dark hospitals (especially for use in Intensive Care Units-IUCs) or nursing home wards, without unnecessary inconvenience to the patient. Provision is made the use of this device during the daytime when illumination would invalidate the use of fluorescence. The solution is a colorimetric, where a simple dye would be used in place of the fluorophore and activating agent. Mere observation of dye in the collection tube during the day time alerts the healthcare professionals to the risk of pressure ulcer formation. The design also accommodates application in patients that are confined to a wheelchair or patients that are upright. As a result of the effect of gravity fluid would not naturally flow into the collection member; for patients in a wheelchair. The issue of flow against gravity is addressed by capillary action; adjusting the inner diameter of the tubing throughout the device compared to the length. For those on a bed, the issue does not arise. The risk is further discussed below, along with the mitigation.

In another embodiment, the fluid is luminol in an alkaline solution and the tube and collection member includes hydrogen peroxide in the presence of iron or copper, or an auxiliary oxidant, produces chemiluminescence. The fluid could include the oxidation of siloxenes, reduction of RuIII complexes by tetrahydridoborate anion, oxidation of lophine, pyrogallol oxidation in the presence of formaldehyde (Trautz-Schorigin reaction), chemiluminescence of singlet oxygen, but arguably the most widespread are activated phenolic oxalates. The reaction of aryl oxalates with hydrogen peroxide (also called peroxyoxalate chemiluminescence) includes a high efficiency of luminesce, long reaction times, and easy color tunability by a judicious choice of fluorescer, spanning from blue to infrared. Examples of phenolic oxalates include DNPO (bis-(2,4-dinitrophenyl)oxalate) and TCPO (bis-(2,4,6-trichlorophenyl)oxalate). Enzymatic chemiluminescent reactions may also be included for the fluid, such as those used in ELISA tests, luciferase, etc.

Others include any chemical or gas that changes colors upon combination or reaction with another chemical and gas, including, but not limited to:

A blue color change of bromothymol blue turning yellow in the presence of the vinegar, but remained blue in the presence of the baking soda.

An iodine clock reaction, which each involve iodine species (iodide ion, free iodine, or iodate ion) and redox reagents in the presence of starch. Two colourless solutions are mixed and at first there is no visible reaction. After a short time delay, the liquid suddenly turns to a shade of dark blue due to the formation of a triiodide-starch complex.

A reaction between two white solids occurs when lead nitrate and potassium iodide are shaken forcefully producing a mixture of yellow and white solid products. The reaction occurs almost instantaneously when aqueous solutions of these compounds are mixed, precipitating yellow lead iodide.

The red color change that occurs when iron (III) thiocyanate complexes that are deep red in color, resembling fake blood.

Colorless to white change that makes a white precipitate by mixing equal amounts of silver nitrate and potassium chloride.

A red color change with the reaction of sodium thiosulfate and hydrochloric acid produces colloidal sulfur which clouds the solution. As the sulfur concentration increases, shorter wavelengths are scattered and longer ones pass through, this causes an increase of reddish color to appear on the overhead.

When you add starch to iodine in water, it creates a starch/iodine complex with an intense blue color.

When copper reacts with the elements (oxygen, water and carbon dioxide), it turns from its element color of reddish-brown to green.

Phenolphthalein stays colorless in acidic solutions and turns pink in alkaline solutions. Sodium hydroxide is a base, so when you add phenolphthalein, the solution turns pink.

In another embodiment, the fluid in the fluid member 110 is a gas. The gas may undergo a chemiluminescent reaction once under the threshold pressure and released into the tube and collection. One gas chemiluminescent reaction is that of elemental white phosphorus oxidizing in moist air, producing a green glow. The moist air would be contained in the fluid member and elemental phosphorus would line the tube member and the collection member. This is a gas-phase reaction of phosphorus vapor, above the solid, with oxygen producing the excited states $(PO)_2$ and HPO. Another gas phase reaction for chemiluminescence is where ozone is combined with nitric oxide to form nitrogen dioxide in an activated state.

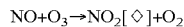

$$NO+O_3 \rightarrow NO_2[\diamond]+O_2$$

The activated $NO_2[\diamond]$ luminesces broadband visible to infrared light as it reverts to a lower energy state. A photomultiplier and associated electronics counts the photons that are proportional to the amount of NO present. To determine the amount of nitrogen dioxide, $NO_2$, in a sample (containing no NO) it must first be converted to nitric oxide, NO, by passing the sample through a converter before the above ozone activation reaction is applied. The ozone reaction produces a photon count proportional to NO that is proportional to $NO_2$ before it was converted to NO. In the case of a mixed sample that contains both NO and $NO_2$, the above reaction yields the amount of NO and $NO_2$ combined in the air sample, assuming that the sample is passed through the converter. If the mixed sample is not passed through the converter, the ozone reaction produces activated $NO_2[\diamond]$ only in proportion to the NO in the sample. The $NO_2$ in the sample is not activated by the ozone reaction. Though unactivated $NO_2$ is present with the activated $NO_2[\diamond]$, photons are emitted only by the activated species that is proportional to original NO.

In one embodiment, the technical specifications of the device prevent further damage to the patient's already compromised skin. Hence, the material selected for the device is Polyvinyl chloride (PVC). PVC is a biocompatible polymer that is used as a biomaterial because of chemical stability and versatility. It was selected because it is used widely for medical tubing, which is one of component members of this design. PVC will also be used for the fluid member and collection member. It meets the need for inertness and durability. It is a suitable material for more delicate biomaterials such as blood bags that need to withstand cracking or leaking. Other biocompatible polymers may be used that does not produce toxin or harmful products and stimulate an immune response in biological systems, including, but not limited to: polyethylene and polypropylene. The biocompatible polymers must include a tensile strength to withstand high pressures of at least 290 lbs/in$^2$, which is about 1.5 times the average body weight.

In one embodiment, the device comprises a sleeve for the fluid member. The device is made of PVC, as discussed previously, for its inertness and biocompatibility, but such a polymer includes a low moisture vapor transmission rate (MVTR). As a result, it is possible that moisture could collect, albeit in small quantities, on the skin of the patient where the device is applied. The collection of moisture on the skin could play a role in further compromising the skin tissue; leaving the patient more susceptible to pressure ulcer and wound formation in condition of shear.

As such, the sleeve or pocket, into which the fluid member can be placed. The sleeve includes a hydrophilic polyurethane dressing. Polyurethane is a material that is already applied in wound healing materials for its high moisture vapor transmission (MVTR), even in wounds that are heavily exuding. The sleeve could contain the whole device to be applied directly to the skin of the patient if necessary because, applied like a band, it would hold the device in place, transmit moisture and sweat away from the skin and prevent the effect of shearing that the device could have on the skin. The sleeve also ensures that the edges of the device, however rough or sharp, do not damage the skin of the patient or compound the problem.

In one embodiment, the attachment mechanism for fastening the device to the clothes, bed or seat of the patient is the use of an adhesive. Coated on sides of the fluid member and collection members, the device can be attached to the patient as needed. In another embodiment, the device is secured in place by elastic band fastened with Velcro fasteners. The elastic band is fitted with a pocket into which the fluid member was placed; allowing the fluid member to remain fixed at the sacral region. This arrangement ensures that even if the patient moves or is moved, the fluid member is not displaced and remains in position. Fastened tightly, the band also prevents the effect of shearing against the skin as the device does not move relative to, or chafe against the patient's skin.

In another embodiment, the attachment mechanism is a sheet. The sheet will be an integration of different embodiments of the device set in pockets of a sheet that the patient lies down or sits on. The units can be arranged and positioned to target and accommodate multiple different pressure injury risk sites. Depending on the sensitivity required, the dimensions of each unit can be varied. The device may be optimized for the sacral region. However, the design of the device is such that it is adjustable to accommodate the needs of each risk site, following the Braden Scale.

In one embodiment, the device will incorporate an electric alert system, such that the nurse can be alerted remotely, without being physically present. Mobile device applications can be involved such that the alerting system is even more convenient for the nurse or caregiver. The device can then be remotely monitored. In one embodiment, the collection member or the tube member is operably coupled with a sensor that detects the changes in the color or Chemiluminescence. The sensor may be an optical sensor, which is an electro-optical sensors are electronic detectors that convert light, or a change in light, into an electronic signal. It measures the physical quantity of light and then translates it into a form that is readable by an instrument. An optical sensor is generally part of a larger system that integrates a source of light, a measuring device and the optical sensor. This is often connected to an electrical trigger. The trigger reacts to a change in the signal within the light sensor. An optical sensor can measure the changes from one or several light beams. When a change occurs, the light sensor operates as a photoelectric trigger and therefore either increases or decreases the electrical output. An optical switch enables signals in optical fibers or integrated optical circuits to be switched selectively from one circuit to another. An optical switch can operate by mechanical means or by electro-optic effects, magneto-optic effects as well as by other methods. Optical switches are optoelectronic devices which can be integrated with integrated or discrete microelectronic circuits. It may be a photoconductive device, photovoltaic, photodiode, or a phototransitor (photo transistor?). The light sensed by the optical sensor may vary in the amount of luminance detected.

Exemplary Dimension Specifications

Figure 9A:
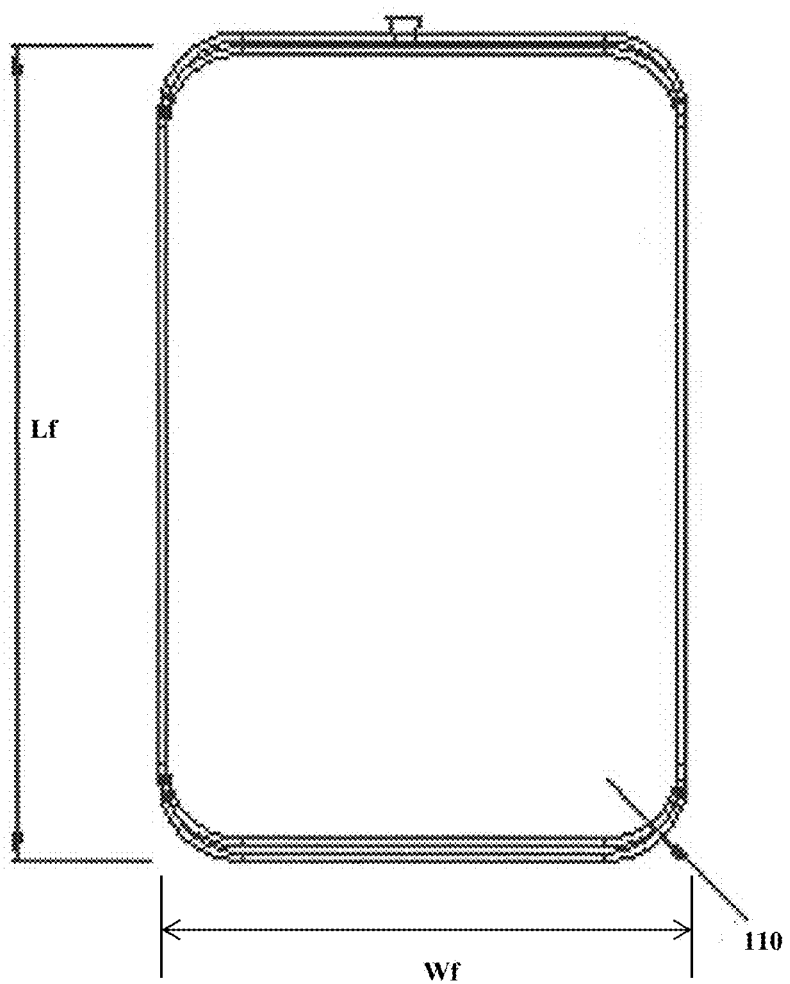
FIG. 9A is a top view of the fluid chamber, according to one embodiment.
Figure 9B:
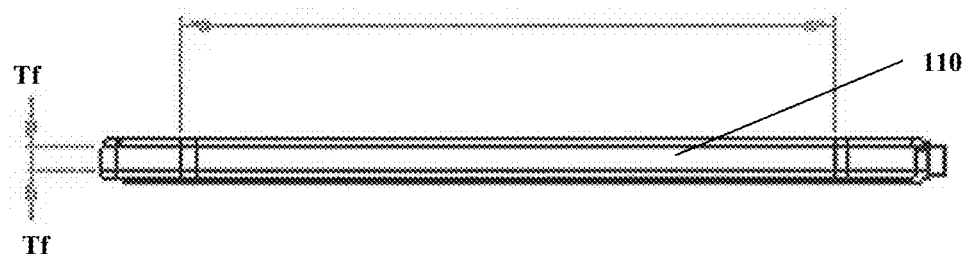
FIG. 9B is a side view of the fluid chamber, according to one embodiment.
Figure 10A:
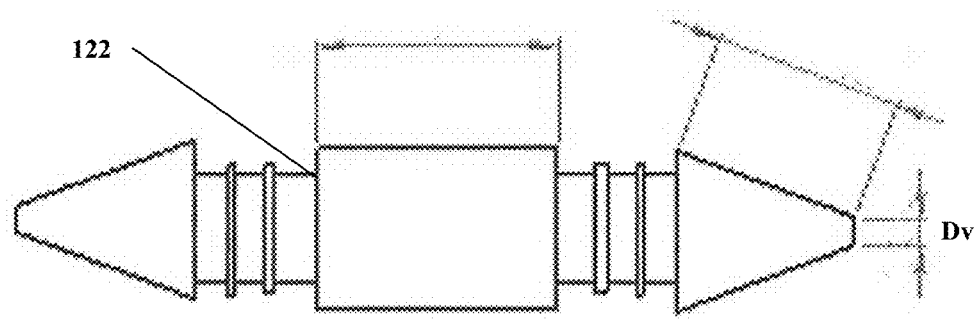
FIG. 10A is a side view of the valve member, according to one embodiment.
Figure 10B:
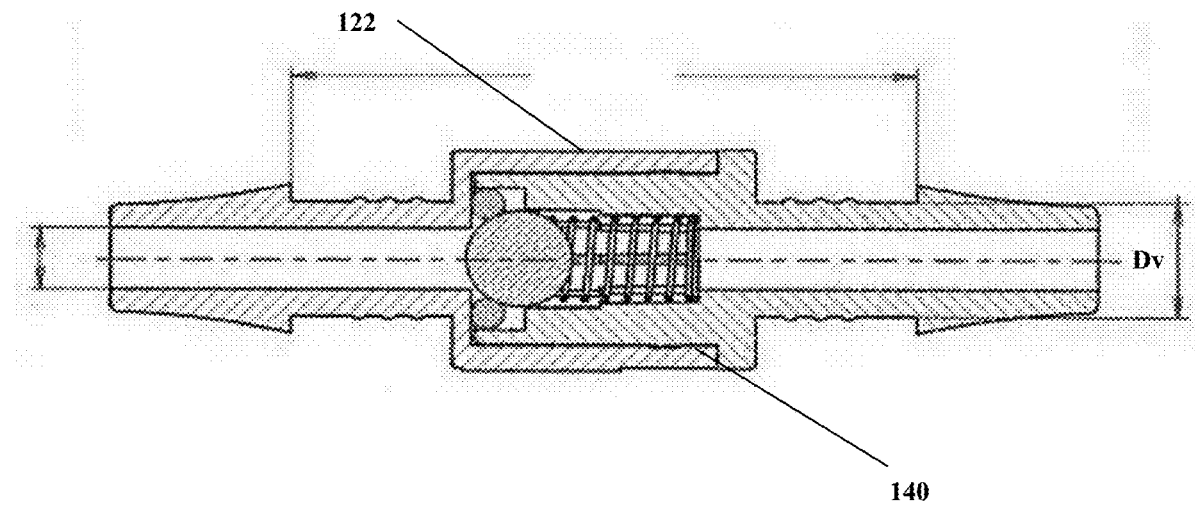
FIG. 10B is a cross-sectional view of the valve member, according to one embodiment.
Figure 11:
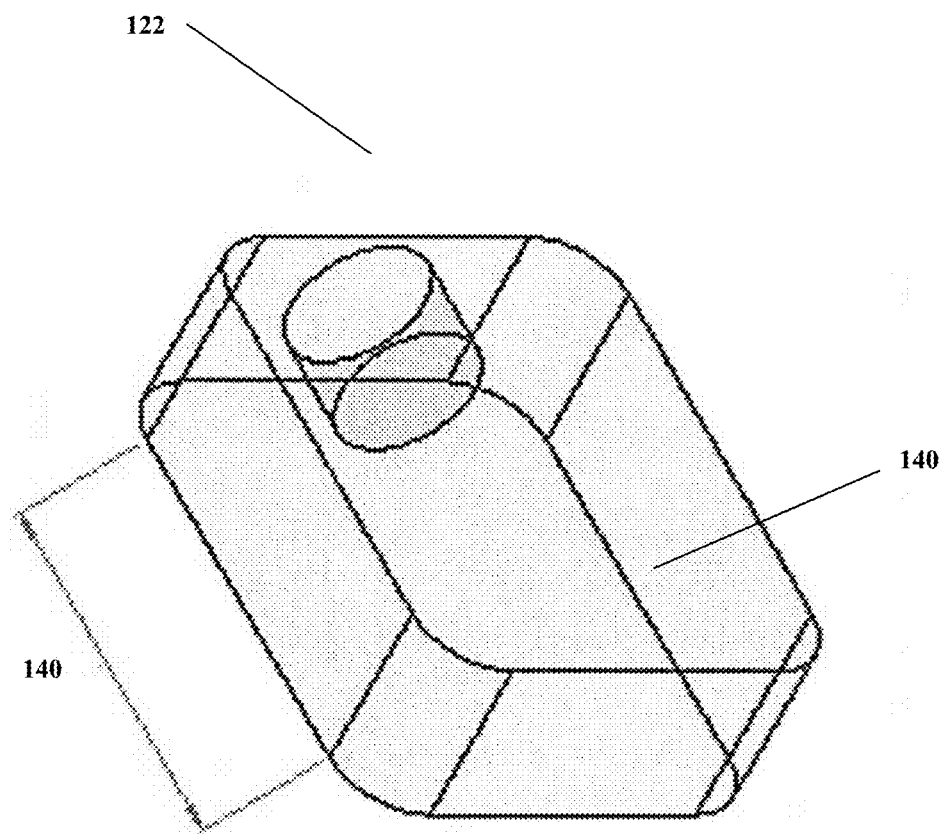
FIG. 11 is a perspective view of the collection member, according to one embodiment.

In one embodiment, the fluid member 110 includes a thickness Tf and a length Lf and a width Wf, as shown in FIGS. 9A & 9B. In one embodiment, the Lf is about 100 mm, Wf is about 65 mm and Tf is about 5 mm; however, these dimensions may be varied according to the particular ulcer prevention and surgical application. For example, the thickness Tf may be varied between about 2 mm to about 20 mm depending on the particular application. The length Lf may be varied between about 10 mm to about 1000 mm. and the width Wf may be varied between about 10 mm to about 1000 mm. In one embodiment, the valve member 122 includes a diameter Dv, as shown in FIGS. 10A-10B. The diameter Dv may be about 4 mm, however it may be varied between 0.1 mm and about 10 mm. The tube member may include a diameter Dt that is substantially equal to the valve member's diameter Dv. As such, the diameter Dt may be about 4 mm, however, it may be varied between 0.1 mm and about 10 mm. The tube member includes a length Lt which may be about 1060 mm however, Lt may be varied between 100 mm and 2000 mm. In one embodiment, the collection member 140 includes a length Lc, which is about 39 mm, as shown in FIG. 11. Alternatively, the collection member includes a radius Rc that is about 25 mm, a thickness Tc about 8 mm, a length Lc about 39 mm, and a height Hc about 46 mm; however, these dimensions may be varied according to the particular ulcer prevention and surgical application. Again, all these dimensions of the device may be varied according to the particular ulcer prevention, location of the device, and surgical application. The exemplary dimensions were selected for one embodiment and can be altered. The diameter of the tube is determined by the dimensions of the first valve member and the second valve member, being the pressure sensing element. The diameter of the tube is very small compared to the length of the tube, which is to implement capillary action that would transmit the fluid against the force of gravity. The diameter of the fluid member is comparable to PVC blood bags. Subsequent dimensions and adjustments would be determined, considering the product specifications listed above. Another major consideration taken in the preliminary dimension specification is the bulkiness of the proposed device and its effect on the comfort of the patient. Hence the fluid member remains thin.

However, because body measurements (especially weight) differ for each patient, the difference would be accommodated by adjusting the volume and surface area of the fluid member. The proposed increase will accommodate higher rate of increase in pressure with time for patients that are heavier, i.e. with a Body Mass Index (BMI) above 25. In one embodiment, the device is intended for application to the buttocks of the patient. But it is versatile in its operation such that it can be applied to the other high risk areas, such as the back of the cranium, the heels and the back of the shoulder blades. Increasing the surface area and volume would also accommodate these bony areas because with a less fat content to cushion against the pressure exerted on the skin, the rate of increase in pressure with time is also increased. The proposed adjustment to the fluid member would first group patients by weight. The surface area and volume of the fluid member would be adjusted to accommodate each weight class and suitable for only the range of weights within the class.

Technical Design

Pressure may be measured for the device and it is calculated by the ratio of force applied to the surface area on which it is applied. The magnitude of pressure and the increase in pressure with time are directly responsible for the formation of pressure ulcers. The pressure equation is also necessary for deciding the weight classing system. Because the surface area of the fluid member of the device and the force applied to that area, affect the response of the first check valve, it is important to match different weights to different fluid member surface areas. Using the same fluid member surface area for different weights (and force applied) will result in skewed readings.

$$P=F/A;$$

Where P=Pressure (mmHg), F=force (kgms−2), A=area (m2).

Hagen-Poiseuille equation:

Hagen Poiseuille's law makes it possible to determine the change in pressure of an incompressible fluid that is flowing in tube of constant cross sectional. But the formula assumes that the fluid flowing in the tube is a Newtonian fluid, the length of the tube is much greater than the diameter and the diameter remains constant throughout the tube. The assumptions made all apply between the fluid member and the inlet of the valve member. The diameter of the tube connecting the fluid member to the inlet of the valve remains constant. However the tube diameter changes after the outlet of the pressure first valve member to become the time second valve and assumptions for Hagen Poiseuille equation no longer hold. It is possible to determine the pressure change between the fluid and valve members and model the flow profile, which become necessary in order to modify, improve or adjust their properties.

$$P=8\mu LQ/(\pi r^2);\ P=128\mu LQ/(\pi d^4);\ P=32\mu Lv/(d^2);$$

Where P=change in pressure (mmHg), L=length (m), =dynamic viscosity (poise) Q=volumetric flow rate (ms-1), r=radius of the tube (m), d=diameter of the tube (m), =pi, v=velocity of flow (ms−1).

Bernoulli's equation:

Per Bernoulli's Principle, the change in potential energy and pressure of a fluid leads to a change in the velocity of flow of the fluid. The reduction in tube diameter in within the tube leading to the collection member serves as the time valve, hence the time is calculated as a function of the change in velocity of fluid flow after the outlet of the second pressure valve. Potential energy in this equation (which occurs as a result of change in height of the fluid vessel) addresses the problem of elevation above, for patients that are seated upright, where the force of gravity restricts fluid flow.

$$(p/\gamma)+(v^2/2g)+z=\text{constant},$$

where p=pressure (mmHg), =specific weight (kgm−2s−2), v=flow velocity (ms−1), z=change in height (m), g=acceleration due to gravity (ms−2).

Figure 5:
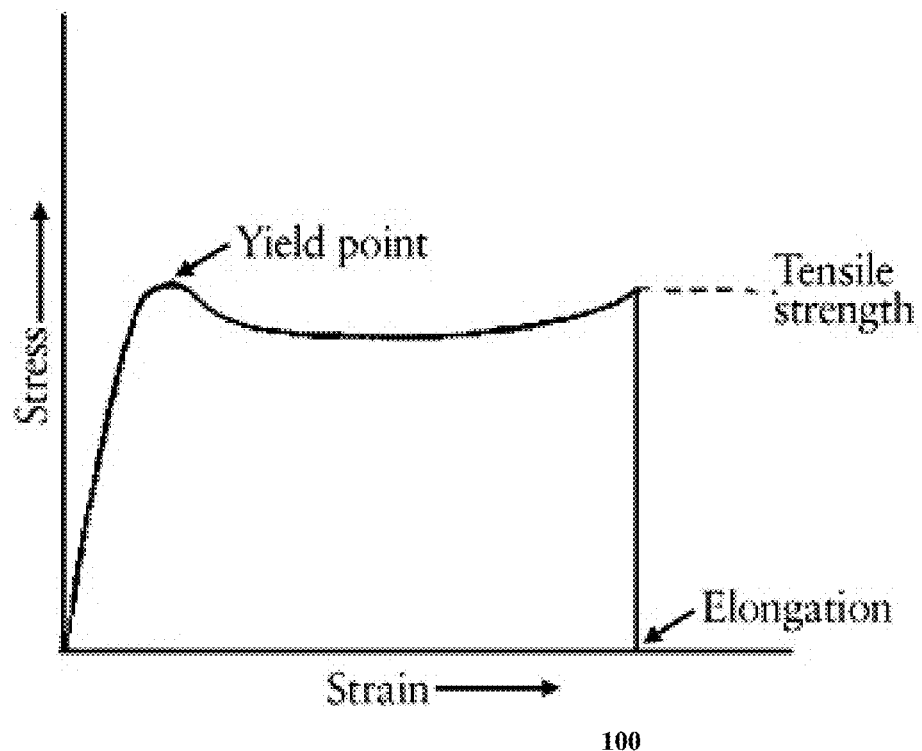
FIG. 5 is a graph showing the relationship between stress and strain for polymers.
Figure 6:
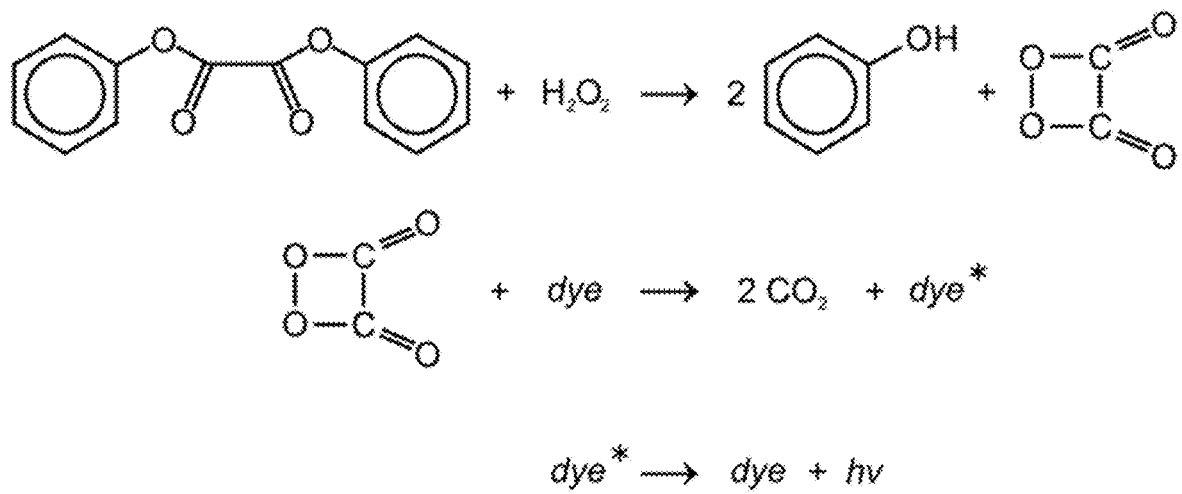
FIG. 6 is a chemical reaction of phenyl oxalate ester and hydrogen peroxide.

Young's Modulus:

Young's modulus gives information on the mechanical properties of the material that is used to construct the device. It describes the ability of the device withstand strain (as a result of being pulled) and stress (as a result of the pressure applied across the surface area of the device). It is also applicable to the mechanical testing of the device, especially for the fluid member, that experiences the greatest external forces. It will help determine the strength of the material and it ability to withstand tensile stresses applied to it. FIG. 5 is a graph showing the relationship between stress and strain for polymers.

$$E = \sigma \varepsilon^{-1}$$

$$\sigma = F/A (\text{stress})(Nm-2)$$

$$\varepsilon = \Delta L/L0 (\text{strain}$$

Chemical reaction of phenyl oxalate ester and hydrogen peroxide is presented in the FIG. 5. In step 1, one mole of phenyl oxalate ester reacted with one mole of hydrogen peroxide to generate 2 moles of phenol and 1 mole of 1,2-dioxetanedione which in turn decomposes to carbon dioxide. The energy released from this reaction excites the dye released from the fluid member (dye*). The excited dye emits light as it relaxes to a stable state.

EXAMPLES

FIG. 7 is a table of the Failure Mode and Effects Analysis showing the risks experienced by the different component parts of the device, and the outcome in probability and severity as those risks are addressed.

FIG. 8 is a table showing the hazards that are posed to the patient as a result of device use and control means.

The shape of the patch or fluid member patch will be analyzed. There is a need for a patch that will not give the patient discomfort since she/he will be in constant contact with the same. Along with the comfort, the fluid member must be able to withstand the weight of the patient without bursting and releasing the fluorophore. The testing plan for this variable will be a compression test that applies a force greater than the one that a person of about 300 lbs will pose on the patch once it's attached to the skin.

The ability of the valves to permit the flow at the specific pressure and time will also be analyzed. Testing plan for this function will be by placing a valve on a tube, and run a fluid at a pressure higher and lower that the one that will be expected to see its function.

Finally, the collecting indicator will be analyzed to make sure that the color of fluorophore has changed. This variable may be tested by placing this indicator in bright light to make sure that regardless of the illumination, the medical professional will be able to distinguish the change in color that will alert that an ulcer is forming.

The failure mode is associated with the seal member component whose function is to detect pressure at a predetermined threshold prior to the formation of irreversible skin damage. The glue in the seal member could be held too loose or too tight resulting in inaccurate pressure sensing. Harsh environmental conditions and contamination could cause the failure. However, the probability of occurrence and remote with a risk level of IV.

Instructions will also include proper handling to prevent from contamination. The device will be inserted directly in the body part needed. It is also disposable lowering the risk of contamination. The packaging will follow strict packaging system performance to validate the capability of the packaging to maintain sterility; stability testing will be performed using real time aging to demonstrate if the sterility will be maintained overtime. The device will comply with FDA standards for packaging and sterility and comply with ISO 11137. To mitigate the risk of harsh environmental conditions interfering with the function of the glue, the device will entail temperature controlled packaging. Instructions on proper storage will also be printed on the label of the device to keep from storage in harsh environmental conditions. The instructions will be printed out in bold red letters to ensure that the user will be able to observe it.

The second risk is possible to occur to the fluid member and the collection member of the device. The fluid member holds the fluid and transmits pressure to the seal member and the collection member holds the released fluid. The risk is associated with a burst or leak of the fluid resulting in inaccurate pressure sensing for the fluid member and no color detection for the collection member of the device. The cause of both failures is attributed to excess weight exerted on the device such as the weight of the patient. However, the severity level is negligible with an improbable occurrence with a total risk level of IV.

The device will come in different sizes and shapes to accommodate for the weight of the patient. A maximum weight capacity will be printed out on the different packaging devices to ensure the mitigation of the risk involved in excess weight leaking the fluids. The excess weight will be lower (~25 lbs) than the tested excess weight to account for scale inconsistencies. For example, if the maximum weight capacity of the device is about 350 lbs, the maximum weight that will be listed on the packaging would be about 325 lbs or a BMI higher than about 25. This can account for improper weighing of the patient and uncertainty of measurement. Additionally, an impact test will be performed where the load will be recorded to detect the failure of the device. This will determine the weight classes.

The tube member acts to transmit fluid to collection. The failure mode involves the inability to transmit against gravity resulting in no color detection. The cause of failure is caused by a patient sitting down (wheelchair), but sitting upright, the fluid will have to flow against gravity to get from the fluid member to the collection over the shoulder. However, the severity level is negligible with an impossible probability of occurrence.

In order to overcome the potential risk, the design of the tube will be altered to a capillary tube. The problem is combatted by adjusting the inner diameter of the tube member. The hydrogen peroxide coating, and the thickness of the tube, allows only a very small diameter within the tube. Hence, by capillary action, and with the coating as a catalyst, the fluid can flow through the tube to the collection member, against gravity; even in an upright patient.

The tube may overcome the inability of the fluid to flow against gravity. The design of the tube will be changed to a smaller diameter of the tube, relative to the length to allow capillary action. Capillary action (sometimes capillarity, capillary motion, capillary effect, or wicking) is the ability of a liquid to flow in narrow spaces without the assistance of, or even in opposition to, external forces like gravity. It occurs because of intermolecular forces between the liquid and surrounding solid surfaces. If the diameter of the tube is sufficiently small, then the combination of surface tension (which is caused by cohesion within the liquid) and adhesive forces between the liquid and container wall act to propel the liquid.

Other risks involved include potential toxicity from fluorophore and PVC, in the unlikely event of ingestion. The packaging will include a label that warns against ingestion and a warning to keep out of reach of children. The label may also include contact information for the poison control center. A hazard symbol will also be included in the packaging as a visual aid.

The device could potentially reduce oxygen supply to the skin. Other materials may be incorporated to eliminate the potential risk of hypoxia. An example of a semi-permeable membrane would be polyurethane foam, which allows the penetration of water vapor and oxygen, and it will simultaneously prevent the penetration of bacteria.

System

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A device for the detection and prevention of pressure ulcers, comprising:
   a fluid chamber operably coupled with a valve member and a tube member, and the fluid chamber including a fluid and the fluid chamber is positioned between a patient and another surface;
   a first pressure valve and a second pressure valve, the first pressure valve configured to open at a pre-determined pressure and conveying fluid through the tube member to the second valve;
   the second valve configured to open at a pre-determined pressure threshold and after a first time period to release the fluid to the tube member; and
   the fluid displays a color once the pre-determined pressure threshold at the second valve is reached and the fluid is released from the second valve.

2. The device of claim 1, wherein the first time period is between about 10 minutes to about 360 minutes.

3. The device of claim 2, wherein the pre-determined pressure threshold of the first valve and the second valve is between about 5 mmHg to about 75 mmHg.

4. The device of claim 3, further comprising: a collection member operably coupled to the tube member and the collection member collects the fluid that chemiluminescences or displays a color once the pressure threshold is reached and the fluid is released from the second valve.

5. The device of claim 4, wherein the fluid member is operably coupled to an attachment mechanism to secure the fluid member to the patient.

6. The device of claim 5, wherein the collection member is operably coupled to an attachment mechanism to secure the collection member to the patient.

7. The device of claim 6, wherein the fluid is a liquid or a gas.

8. The device of claim 7, wherein the liquid includes a chemical that undergoes chemiluminescence.

9. The device of claim 6, wherein the valve member is operably coupled to an alarm system.

10. The device of claim 6, further comprising a fluid dam separating the fluid in the fluid member from the tube member, wherein the fluid dam opens to release the fluid at a predetermined pressure and a time value.

11. The device of claim 5, wherein the attachment mechanism is a sheet.

12. A method for the detection and prevention of pressure ulcers, comprising:
    Coupling a fluid chamber with a valve member and a tube member, and positioning the fluid chamber including a fluid between a patient and another surface;
    Releasing the fluid from the valve member at a pressure threshold and after a first time period to the tube member; and
    Displaying a color in the tube member to prevent pressure ulcers from being developed.

13. The method of claim 12, wherein the first time period is between about 10 minutes to about 360 minutes.

14. The method of claim 13, wherein the pressure threshold is between about 5 mmHg to about 75 mmHg.

15. The method of claim 13, further comprising: coupling a collection member to the tube member and the collection member collects the fluid that changes color.

16. The method of claim 15, wherein the valve member including a first valve and a second valve, wherein the first valve opens as fluid pressure builds within the fluid chamber, the first valve releasing the fluid through the tube member to the second valve at a pressure threshold.

17. The device of claim 16, wherein the fluid is a liquid or a gas.

18. The device of claim 17, wherein the liquid includes a chemical that undergoes chemiluminescence.

19. The device of claim 16, further comprising coupling an alarm system with the valve member to prevent pressure ulcers from being developed.

20. The device of claim 15, further comprising separating the fluid in the fluid member from the tube member with a fluid dam, wherein the fluid dam opens to release the fluid at a predetermined pressure and a time value.

* * * * *